(12) United States Patent
Domloge et al.

(10) Patent No.: US 9,364,414 B2
(45) Date of Patent: Jun. 14, 2016

(54) METHOD TO PROTECT SKIN FROM ULTRAVIOLET RADIATION USING NOVEL PEPTIDES INVOLVED IN THE IMPROVEMENT OF MICROPARASOL ORGANIZATION IN KERATINOCYTES

(71) Applicant: ISP Investments Inc., Wilmington, DE (US)

(72) Inventors: Nouha Domloge, Valbonne (FR); Jean-Marie Botto, Valbonne (FR); Catherine Serre, Roquefort les Pins (FR); Alexia Lebleu, Cagnes sur Mer (FR)

(73) Assignee: ISP INVESTMENTS INC., Wilmington, DE (US)

( * ) Notice: Subject to any disclaimer, the term of this patent is extended or adjusted under 35 U.S.C. 154(b) by 0 days.

(21) Appl. No.: 14/569,144

(22) Filed: Dec. 12, 2014

(65) Prior Publication Data

US 2015/0093342 A1 Apr. 2, 2015

Related U.S. Application Data

(63) Continuation-in-part of application No. 13/982,386, filed as application No. PCT/FR2012/000035 on Jan. 30, 2012, now Pat. No. 8,962,565.

(30) Foreign Application Priority Data

Feb. 1, 2011 (FR) ...................................... 11 00299

(51) Int. Cl.
| | | |
|---|---|---|
| *A61K 8/64* | (2006.01) | |
| *A61Q 19/02* | (2006.01) | |
| *A61Q 19/04* | (2006.01) | |
| *A61Q 19/08* | (2006.01) | |
| *A61Q 17/04* | (2006.01) | |

(52) U.S. Cl.
CPC . *A61K 8/64* (2013.01); *A61Q 19/02* (2013.01); *A61Q 19/08* (2013.01); *A61K 2800/522* (2013.01); *A61K 2800/78* (2013.01)

(58) Field of Classification Search
CPC .................. A61K 2800/522; A61K 2800/78; A61K 8/64; A61Q 19/02; A61Q 19/08

USPC ....................................................... 424/59, 62
See application file for complete search history.

(56) References Cited

U.S. PATENT DOCUMENTS

| | | |
|---|---|---|
| 6,919,187 B2 | 7/2005 | Bhatia et al. |
| 7,300,918 B2 | 11/2007 | Rath |
| 8,440,881 B2 | 5/2013 | Park et al. |
| 2002/0146776 A1 | 10/2002 | Bhatia et al. |
| 2011/0311538 A1 | 12/2011 | Schlessinger et al. |
| 2013/0333061 A1 | 12/2013 | Wu et al. |
| 2014/0010861 A1 | 1/2014 | Bancel et al. |
| 2014/0106981 A1 | 4/2014 | Hood et al. |
| 2014/0130203 A1 | 5/2014 | La Rosa et al. |

FOREIGN PATENT DOCUMENTS

| | | | |
|---|---|---|---|
| JP | 2008-031094 | 2/2008 | |
| WO | 93/20210 | 10/1993 | |
| WO | 01/31019 | 5/2001 | |
| WO | WO 2006/004341 | * 1/2006 | ............. G01N 33/68 |
| WO | 2010/037395 | 4/2010 | |

OTHER PUBLICATIONS

X1WV47_ACYPI from UniProtKB, http://www.unitprot.org/uniprot/X1WV47, pp. 1-4. Accessed Nov. 6, 2015.*
PCT, International Search Report, International Application No. PCT/FR2012/000035 (mailed Jun. 5, 2012, published Aug. 9, 2012).
Office Action issued for U.S. Appl. No. 13/982,386 on Jul. 8, 2014.
Notice of Allowance issued for U.S. Appl. No. 13/982,386 on Nov. 7, 2014.

* cited by examiner

*Primary Examiner* — Julie Ha
(74) *Attorney, Agent, or Firm* — Thompson Hine LLP (57) ABSTRACT

Cosmetic methods for improving the microparasol organization in keratinocytes, protecting skin against ultraviolet radiation, decreasing DNA photodamage in keratinocytes and melanocytes, attenuating age-related pigmentation defects and the effects of photoaging on the skin are described. The methods include applying a composition comprising a peptide compound of one of SEQ ID NO: 1, SEQ ID NO: 2, SEQ ID NO: 3, SEQ ID NO: 4, SEQ ID NO: 5, SEQ ID NO: 6, or SEQ ID NO: 7, and a cosmetically acceptable medium to appendages or to the affected skin of a subject in need thereof.

10 Claims, 4 Drawing Sheets

Figure 1: Effect of peptide compound SEQ ID NO: 7 on keratinocytes containing melanosomes after treatment with p150Glued siRNA (mean ± sem; n=3; ***: highly significant, *: significant, ns: no significant, with Student's t-test).

Figure 2a: Comet assay on NHK treated with the peptide SEQ ID NO: 7 at 1% (referred to herein as IV09.007) and irradiated with UVB radiation Figure 2b: Comet assay on NHEM treated with the peptide SEQ ID NO: 7 (referred to herein as IV09.007) and irradiated with UVB radiation Figure 3: Effect of peptide compound SEQ ID NO: 7 on the amount of CPD in melanocytes after 48 hours.

(mean ± sem; n=3, *** highly significant, *: significant, with Student's $t$-test).

SEQUENCE LISTING

```
<160> NUMBER OF SEQ ID NOS: 7

<210> SEQ ID NO 1
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (8)..(8)
<223> OTHER INFORMATION: AMIDATION

<400> SEQUENCE: 1

Ser Cys Arg Asp Leu Lys Lys Thr
1               5

<210> SEQ ID NO 2
<211> LENGTH: 11
<212> TYPE: PRT
<213> ORGANISM: Artificial Sequence
<220> FEATURE:
<223> OTHER INFORMATION: Synthetic peptide

<400> SEQUENCE: 2

Asn Ser Ser Lys Asp Leu Lys Lys Phe Val Ala
```

```
1               5                    10

<210> SEQ ID NO 3
<211> LENGTH: 8
<212> TYPE: PRT
<213> ORGANISM: Artificial Sequence
<220> FEATURE:
<223> OTHER INFORMATION: Synthetic peptide

<400> SEQUENCE: 3

Cys Lys Asp Leu Lys Lys Ser Phe
1               5

<210> SEQ ID NO 4
<211> LENGTH: 11
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (11)..(11)
<223> OTHER INFORMATION: AMIDATION

<400> SEQUENCE: 4

Gln Thr Arg Asp Leu Lys Lys Ser Pro Lys Val
1               5                   10

<210> SEQ ID NO 5
<211> LENGTH: 8
<212> TYPE: PRT
<213> ORGANISM: Artificial Sequence
<220> FEATURE:
<223> OTHER INFORMATION: Synthetic peptide

<400> SEQUENCE: 5

Asn Lys Asp Leu Lys Lys Pro Met
1               5

<210> SEQ ID NO 6
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (6)..(6)
<223> OTHER INFORMATION: AMIDATION

<400> SEQUENCE: 6

His Asp Leu Lys Lys Tyr
1               5

<210> SEQ ID NO 7
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (4)..(4)
<223> OTHER INFORMATION: AMIDATION

<400> SEQUENCE: 7

Asp Leu Lys Lys
1
```

METHOD TO PROTECT SKIN FROM ULTRAVIOLET RADIATION USING NOVEL PEPTIDES INVOLVED IN THE IMPROVEMENT OF MICROPARASOL ORGANIZATION IN KERATINOCYTES

RELATED APPLICATIONS

This application is a continuation-in-part of U.S. application Ser. No. 13/982,386, filed Jul. 29, 2013 (now U.S. Pat. No. 8,962,565), which was the National Stage of International Application No. PCT/FR2012/000035, filed Jan. 30, 2012, which claims priority of French Patent Application No. 1100299, filed Feb. 1, 2011, the entire contents of which are incorporated herein by reference.

TECHNICAL FIELD

This invention relates to the fields of cosmetics and pharmacy. It relates to peptide compounds with the following general formula (I):

$R_1\text{-}(AA)_n\text{-}X_1\text{---}X_2\text{---}X_3\text{-}Asp\text{-}Leu\text{-}Lys\text{-}Lys\text{-}X_4\text{---}X_5\text{-}(AA)_p\text{-}R_2$ as a compound having an action on the SCF/c-Kit signaling pathway and on the dynactin subunit p150Glued, as well as its uses in cosmetic and/or pharmaceutical compositions in order to attenuate skin pigmentation defects.

BACKGROUND

In humans, hair and skin color is related to individual factors (ethnic origin, sex, age, etc.) and environmental factors (in particular the seasons of the year, region inhabited, etc.). It is primarily determined by the nature and concentration of melanin produced by the melanocytes. The melanocytes are large dendritic cells located in the basal layer of the epidermis. These specialized cells will, by way of specific organites, the melanosomes, synthesize melanin. The synthesis of melanin or melanogenesis is a complex process of which the precise mechanisms are not yet understood, and which schematically involves the following steps:

This melanin plays a fundamental role in the determination of skin color. We often hear of epidermal (or elementary) melanization units that correspond in fact to functional groups in which the melanocytes maintain contact with a certain number of neighboring keratinocytes, to which they transfer the pigment grains. The number of units varies according to the body region. These units contain, on average, 1 melanocyte for 36 keratinocytes (although there are variations). The transfer of pigment from the melanocyte to the keratinocytes occurs in 4 main steps:

1: synthesis of the melanosomes in the melanocyte;
2: melanization of the melanosomes in the melanocyte;
3: transfer of the melanosomes to the keratinocytes;
4: degradation and elimination of melanosomes in the keratinocytes.

As the melanin is synthesized in the melanosomes, they move from the perinuclear region to the end of the dendrites of the melanocytes. By phagocytosis, the end of the dendrites is captured by the keratinocytes, the membranes are degraded and the melanosomes are redistributed in the keratinocytes. Once in the keratinocytes, the melanosomes are distributed according to their size: in isolation for the largest ones, in groups for the smallest ones (Ortonne, et al. 1981). They are secondarily degraded in lysosomal vacuoles (Fitzpatrick et al. 1979).

The transfer of melanosomes to the keratinocytes, as described above, is performed by means of numerous biological, enzymatic processes, and is not currently fully understood. One of the players in this melanosome transfer process is SCF protein and its c-Kit receptor. The SCF (Stem Cell Factor) protein is the natural agonist ligand of the c-Kit receptor, which is a member of the sub-family III of the superfamily of receptor tyrosine kinases (RTK). It has been demonstrated in numerous publications that this SCF/c-Kit signaling pathway played a key role in a number of biological processes, and in particular in hematopoiesis, spermatogenesis, as well as in the maintenance of homeostasis of the skin and in the pigmentation of same (Longley J. et al, *J Invest Dermatol.* 1999; 113: 139-140).

It is known that anomalies in the transfer of melanosomes to the keratinocytes can lead to pigmentation disorders, whether of the hyperpigmentation or the hypopigmentation type. More specifically, certain studies have shown that the SCF/c-Kit signaling pathway could regulate both the proliferation and the differentiation of melanocytes. The SCF protein at the surface of the epidermal keratinocytes could enable regulation of the adjacent melanocytes, via direct interaction with the c-Kit receptor located on said melanocytes. Moreover, it has been demonstrated that certain transcription factors crucial for the synthesis of melanin were activated by the SCF/c-Kit pathway (Grichnik, J M et al. *J Invest Dermatol.* 1998; 111: 233-238). It can therefore be considered that the SCF/c-Kit pathway is important for the normal function of melanocytes, and that it is possible for alterations at the level of this signaling pathway are responsible for certain melanocyte disorders, i.e. pigmentation disorders.

Once within keratinocytes, melanosomes are gradually distributed to the perinuclear area. Then melanosomes densely aggregate above the nucleus in a supranuclear cap called "microparasol" in suprabasal keratinocytes. This positioning of melanosomes above the nucleus serves as a protective mechanism shielding the keratinocyte nucleus from harmful ULTRAVIOLET radiations. Both the transfer of melanosomes from melanocytes to keratinocytes and the distribution of melanosomes into microparasols are processes dependent on the movement of these organelles along microtubules. Such movements of melanosomes involve the molecular motor proteins kinesin and dynein. Cytoplasmic dynein is a multisubunit complex consisting of two heavy chains and several intermediate/light and light chains. The heavy chains contain sites for microtubule binding and ATP hydrolysis whereas the remaining subunits may contain recognition binding sites for organelles. Dynein associates with its cargoes through a complex called "dynactin complex" (Byers H R, Maheshwary S, Amodeo D M & Dystra S G. Role of cytoplasmic dynein in perinuclear aggregation of phagocytosed melanosomes and supranuclear melanin cap formation in human keratinocytes. J Invest Dermatol (2003) 121: 813-820).

In keratinocytes, dynactin p150Glued subunit acts as a "dynein anchor" and plays a role in the capture and centripetal transport of melanosomes to the perinuclear area of keratinocytes. Moreover, this protein is involved in the formation and maintenance of microparasols. Furthermore, major damages of microparasol structural and functional integrity have been observed after knockdown of p150Glued by siRNA (Alexia Lebleu et al. Maintenance of keratinocytes "microparasol" by targeting p150glued dynactin subunit, IFSCC Conference 2013. Book of Abstracts; 061:150-152).

Along with SCF/c-Kit signaling pathway, the integrity of microparasols is essential to prevent DNA photodamage of cutaneous cells.

SUMMARY

Along this line of research, the Applicant demonstrated that peptide compounds of the following general formula (I):

(I)

were agents making it possible to influence the pigmentation of the skin and skin appendages, by ensuring optimal transfer of the melanosomes to the keratinocytes and improvement of microparasol organization in keratinocytes, so as to make the skin tone uniform owing to an effect on both the SCF/c-Kit signaling pathway and the dynactin subunit p150Glued.

The peptide compounds according to the invention are characterized by the fact that they:
- protect the pigment structures of the skin from external stresses;
- improve microparasol organization in keratinocytes
- make it possible to attenuate age-related pigmentation defects as well as the effects of photoaging on the skin; and
- make it possible to treat skin tone irregularities and unify skin tone.

This invention therefore relates firstly to a peptide compound with the following general formula (I):

(I)

This invention relates secondly to a cosmetic composition comprising, as an active ingredient, said peptide compound of formula (I).

In addition, this invention relates thirdly to the use of a cosmetic composition comprising said peptide compound of formula (I) in order (i) to protect the skin pigment structures from external stresses, (ii) to attenuate age-related pigmentation defects and the effects of photoaging on the skin, and (iii) to treat skin tone irregularities and unify skin tone.

Finally, this invention relates to methods for cosmetic treatment of the skin or skin appendages to be treated by means of the composition comprising said peptide compound of formula (I).

DETAILED DESCRIPTION

This invention relates, firstly, to a peptide compound of general formula (I):

(I)

wherein,
$X_1$ represents an asparagine, a serine, a glutamine or no amino acid,
$X_2$ represents a serine, a threonine, a cysteine or no amino acid,
$X_3$ represents an arginine, a lysine, a histidine or no amino acid,
$X_4$ represents a serine, a tyrosine, a threonine or no amino acid,
$X_5$ represents a phenylalanine, a proline, an alanine, a valine or no amino acid,
AA represents any amino acid, and n and p are integers between 0 and 2,
$R_1$ represents the primary amino function of the N-terminal amino acid, —$NH_2$, wherein one of the two hydrogen atoms can be substituted either by a $C_1$ to $C_{30}$ saturated or unsaturated alkyl chain of the acetyl type, or by an aromatic group of the benzoyl, tosyl or benzyloxycarbonyl type.
$R_2$ represents the hydroxyl group of the carboxyl function of the C-terminal amino acid, —OH, wherein the hydrogen atom can be substituted by a $C_1$ to $C_{30}$ alkyl chain, or an $NH_2$, NHY or NYY group, in which Y represents a $C_1$ to $C_4$ alkyl chain,
said sequence of general formula (I) consisting of 4 to 13 amino acid residues.

The term "peptide compound" or "peptide" refers to a chain of two or more aminoacids bound together by peptide bonds or by modified peptide bonds.

"Peptide compound" or "peptide" should be understood to mean the natural or synthetic peptide of the invention as described above, or at least one of its fragments, whether it is obtained by proteolysis or synthetically, or any natural or synthetic peptide of which the sequence consists entirely or partially of the sequence of the aforementioned peptide.

The amino acids constituting the peptide compound according to the invention can be in a levorotatory configuration, i.e. L-, and/or a dextrorotatory configuration, i.e. D-. The peptide according to the invention can therefore be in L-, D- or DL-form.

To improve resistance to degradation, it may be necessary to use a protected form of the peptide according to the invention. The form of protection must obviously be a biologically compatible form and must be compatible with a use in the fields of cosmetics and pharmacy. Preferably, to protect the primary amine function of the N-terminal amino acid, a substitution by an $R_1$ group of the acyl type having a saturated or unsaturated $C_1$ to $C_{30}$ alkyl chain, capable of being chosen from an acetyl group or an aromatic group, is used. Preferably, to protect the carboxyl function of the C-terminal amino acid, a substitution by an $R_2$ group of the $C_1$ to $C_{30}$ alkyl chain type or an $NH_2$, NHY or NYY group with Y representing a $C_1$ to $C_4$ alkyl chain.

The peptide according to the invention can be protected at the N-terminal end, the C-terminal end or at both ends.

In a first embodiment of the invention, in general formula (I), n and p are equal to zero and the sequence of general formula (I) consists of 4 to 9 amino acid residues. This therefore means that, in general formula (I):
$X_1$ represents an asparagine, a serine, a glutamine or no amino acid,
$X_2$ represents a serine, a threonine, a cysteine or no amino acid,
$X_3$ represents an arginine, a lysine, a histidine or no amino acid,
$X_4$ represents a serine, a tyrosine, a threonine or no amino acid,
$X_5$ represents a phenylalanine, a proline, an alanine, a valine or no amino acid, the integers n and p are equal to zero,
$R_1$ represents the primary amine function of the N-terminal amino acid, —$NH_2$, wherein one of the two hydrogen atoms can be substituted either by a saturated or unsaturated $C_1$ to $C_{30}$ alkyl chain of the acetyl type, or by an aromatic group of the benzoyl, tosyl or benzyloxycarbonyl type, $R_2$ represents the hydroxyl group of the carboxyl function of the C-terminal amino acid, —OH, wherein the hydrogen atom can be substituted by a $C_1$ to $C_{30}$ alkyl chain, or an $NH_2$, NHY or NYY group, wherein Y represents a $C_1$ to $C_4$ alkyl chain, said sequence of general formula (I) consisting of 4 to 9 amino acid residues.

In a second preferred embodiment, the peptide compound corresponds to one of the following formulas:

```
                                              (SEQ ID NO: 1)
Ser-Cys-Arg-Asp-Leu-Lys-Lys-Thr-NH2

(SEQ ID NO: 2)
Asn-Ser-Ser-Lys-Asp-Leu-Lys-Lys-Phe-Val-Ala (SEQ ID NO: 3)
Cys-Lys-Asp-Leu-Lys-Lys-Ser-Phe (SEQ ID NO: 4)
Gln-Thr-Arg-Asp-Leu-Lys-Lys-Ser-Pro-Lys-Val-NH2

(SEQ ID NO: 5)
Asn-Lys-Asp-Leu-Lys-Lys-Pro-Met (SEQ ID NO: 6)
His-Asp-Leu-Lys-Lys-Tyr-NH2

(SEQ ID NO: 7)
Asp-Leu-Lys-Lys-NH2
```

The invention also relates to homologous forms of these sequences. The term "homologous" refers, according to the invention, to any peptide sequence identical to at least 50%, or preferably at least 80%, and even more preferably to at least 90% of said peptide sequence, chosen from sequences SEQ ID NO: 1 to SEQ ID NO: 7. "Peptide sequence identical to at least X %" means a percentage of identity between the amino acid residues of the two sequences to be compared, obtained after optimal alignment of the two sequences. The optimal alignment is obtained by means of local homology algorithms such as those used by the BLAST P computer software program available at the NCBI site.

The term "homologous" can also refer to a peptide that differs from the sequence of a peptide of sequence SEQ ID NO: 1 to SEQ ID NO: 7 by the substitution of chemically equivalent amino acids, i.e. by the substitution of a residue by another one having the same characteristics. Thus, the classic substitutions are made between Ala, Val, Leu and Ile; between Ser and Thr; between the acid residues Asp and Glu; between Asn and Gln; and between the basic residues Lys and Arg; or between the aromatic residues Phe and Tyr.

The peptide of general formula (I) according to the invention can be obtained either by classic chemical synthesis (in solid phase or in homogeneous liquid phase), or by enzymatic synthesis (Kullmann et al., J. Biol. Chem. 1980; 225: 8234) using its constituent amino acids or derivatives.

The peptide according to the invention can be of natural or synthetic origin. Preferably, according to the invention, the peptide is obtained by chemical synthesis.

Finally, the active ingredient can be a single peptide, a mixture of peptides or peptide derivatives and/or consist of amino acid derivatives.

The peptide compound according to the invention can be used as a drug.

According to an advantageous embodiment of the invention, the peptide compound according to the invention is solubilized in one or more physiologically suitable solvents, classically used by a person skilled in the art, such as water, glycerol, ethanol, propanediol, butylene glycol, dipropylene glycol, ethoxylated or propoxylated diglycols, cyclic polyols, or any mixture of these solvents.

According to yet another advantageous embodiment of the invention, the peptide compound according to the invention is solubilized in a cosmetic or pharmaceutical vector such as liposomes, or adsorbed on powdery organic polymers, mineral supports such as talcs and bentonites, and more generally solubilized in, or fixed on, any physiologically suitable vector.

This invention relates, secondly, to a cosmetic composition comprising, as an active ingredient, said peptide compound of general formula (I).

Preferably, the compositions according to the invention are in a form suitable for topical application comprising a cosmetically acceptable medium. By "cosmetically acceptable", we mean media that are suitable for use in contact with the skin or human skin appendages, without risk of toxicity, incompatibility, instability, allergic response or the like. The compositions intended to be applied to the skin can be in the form of a cream, an oil-in-water emulsion, or a water-in-oil or multiple emulsion, a solution, a suspension, a microemulsion, an aqueous or anhydrous gel, a serum, or a vesicle dispersion, a patch, a spray, an ointment, a pomade, a lotion, a colloid, a milk, a lotion, a stick or a powder, all suitable for application on the skin, lips and/or skin appendages.

Preferably, said peptide compound is present in the composition at a concentration of between around 0.0005 and 500 ppm, and preferably at a concentration of between 0.01 and 5 ppm.

Even more preferably, the composition according to the invention also contains at least one additional active ingredient. It is possible to cite, in a non-limiting manner, the following classes of ingredients:

sunscreens, ultraviolet and infrared screens anti-free radical agents,

DHEA (dehydroepiandrosterone),—vitamin A and notably retinoic acid, retinol, retinol proprionate, retinol palmitate, vitamin B3 and notably niacinamide, niconitate of tocopherol, vitamin B5, vitamin B6, vitamin B12, panthenol, vitamin C, and notably ascorbic acid, ascorbyl glucoside, ascorbyl tetrapalmitate, magnesium and sodium ascorbyl phosphate, vitamins E, F, H, K, PP, and coenzyme Q10, metalloproteinase inhibitor, activator of TIMP, aminoacids and notably arginine, ornithine, hydroxyproline, hydroxyproline dipalmitate, palmitoylglycine, hydroxylysine, methionine and its derivatives, N-acylated aminoacids, natural or synthetic peptides, including, di-, tri-, tetra-, penta- and hexapeptides and their lipophilic derivatives, isomers and complex with other molecules such as metallic ion (i.e. copper, zinc, manganese, magnesium, and others), peptides sold under commercial names MATRIXYL®, ARGIRELINE®, COLLAXYL™, PEPTIDE VINCI 02™, CHRONOGEN™, LAMINIXYL IS™, PEPTIDE Q10™, peptidic plant extracts obtained by hydrolysis or any other methods such as soy extract, einkorn extract, *vitis vinifera* extract, rapeseed extract, flaxseed extract rice extract, corn extract, or pea extract, carob extract, bean extract, fava extract, yeast extract, *artemia salina* extract, dehydroacetic acid (DHA), natural or synthetic phytosterols, alpha- and beta-hydroxyacids, silanols, sugar amines, glucosamine, D-glucosamine, N-acetyl-glucosamine, N-acetyl-D-glucosamine, mannosamine, N-acetyl mannosamine, galactosamine, N-acetyl galactosamine, polyphenols, isoflavones, flavonoids, such as grape extract, pine extract, olive extract, lipids such as ceramides or phospholipids, animal oils such as squalenes or squalanes, vegetal oils, such as almond oil, coconut oil, castor oil, jojoba oil, olive oil, rapeseed oil, peanut oil, sunflower oil, wheat germ oil, corn germ oil, soybean oil, cotton oil, alfalfa oil, poppy oil, pumpkin seed oil, evening primrose oil, millet oil, barley oil, rye oil, safflower oil, passion oil, hazelnut oil, palm oil, apricot kernel oil, avocado oil, calendula oil, ethoxylated vegetable oils, or shea butter, Said compounds above can be natural, such as plant peptide hydrolysates, or of synthetic origin, such as peptide compounds.

In addition, additives such as solvents, diluents, dyes, sunscreens, self-tanning agents, pigments, fillers, preservatives, odor absorbents, thickening agents, emulsifiers, moistening agents, emollients, fragrances, antioxidants, film-forming agents, chelating agents, sequestering agents and conditioners can be added to the composition.

In every case, a person skilled in the art will make sure that these adjuvants as well as the proportions thereof are chosen so as not to adversely affect the desired advantageous properties of the composition according to the invention. These adjuvants can be, for example, between 0.01 and 20% of the total weight of the composition. When the composition of the invention is an emulsion, the fatty phase can be 5 to 80% by weight, and preferably 5 to 50% by weight with respect to the total weight of the composition. The emulsifiers and co-emulsifiers used in the composition will be chosen among those classically used in the field considered. For example, they may be used in a proportion ranging from 0.3 to 30% by weight with respect to the total weight of the composition.

The invention relates, thirdly, to the use of a cosmetic composition comprising said peptide compound in a cosmetically acceptable medium for protecting skin pigment structures from external stresses. By "pigment structures", we mean the melanocytes and keratinocytes maintaining contact with one another and forming an epidermal (or elementary) melanization unit (more precisely one melanocyte for 36 keratinocytes, on average).

By "external stresses", we mean stresses that the environment may product. For example, it is possible to cite stresses such as pollution, ultraviolet radiation, stresses causing oxidative stress, or irritating products such as surfactants, preservatives or fragrances, mechanical stresses, such as abrasions, shaving or hair removal. However, preferably, the external stresses consist primarily of ultraviolet radiation, and in particular UVB radiation, and the stresses causing oxidative stress.

Another use of the peptide according to the invention consists of attenuating age-related pigmentation defects and the effects of photoaging on the skin. By "photoaging", we mean premature skin aging caused by prolonged and cumulative exposure to the sun. By "age-related pigmentation defects", we mean age spots, solar lentigines, depigmentation spots or freckles. To this effect, the peptide according to the invention may be used to treat skin tone irregularities and unify skin tone.

The invention relates fourthly, to a method for cosmetic treatment characterized by applying, in the morning or the evening, on the skin, a composition comprising the peptide according to the invention in order to attenuate age-related pigmentation defects and the effects of photoaging on the skin. A first embodiment consists of applying said composition either before sun exposure (i.e. before ultraviolet radiation exposure), as before-sun care, or after sun exposure (i.e. after ultraviolet radiation exposure), as after-sun care, in order (i) to prevent and/or repair damage due to ultraviolet radiation on the skin cells and (ii) to limit the appearance of hyperpigmentation spots, solar lentigines, depigmentation spots, or freckles.

The invention relates fifthly to a cosmetic method for improving microparasol organization in keratinocytes, the method comprising applying on the skin or the skin appendages to be treated, a composition comprising a peptide compound having one of the following sequences:

```
                                        (SEQ ID NO: 1)
Ser-Cys-Arg-Asp-Leu-Lys-Lys-Thr-NH2;
or
                                        (SEQ ID NO: 2)
Asn-Ser-Ser-Lys-Asp-Leu-Lys-Lys-Phe-Val-Ala-NH2;
or
                                        (SEQ ID NO: 3)
Cys-Lys-Asp-Leu-Lys-Lys-Ser-Phe;
or
                                        (SEQ ID NO: 4)
Gln-Thr-Arg-Asp-Leu-Lys-Lys-Ser-Pro-Lys-Val-NH2;
or
                                        (SEQ ID NO: 5)
Asn-Lys-Asp-Leu-Lys-Lys-Pro-Met;
or
                                        (SEQ ID NO: 6)
His-Asp-Leu-Lys-Lys-Tyr-NH2;
or
                                        (SEQ ID NO: 7)
Asp-Leu-Lys-Lys-NH2,
and
``` a cosmetically acceptable medium.

By "microparasol organization in keratinocytes" we mean the supranuclear cap of melanosomes assembled above the nucleus of keratinocytes.

The invention relates sixthly to a cosmetic method wherein applying the composition protects the treated skin or the treated skin appendages against ultraviolet radiation.

The invention relates lastly to a method for decreasing DNA damages caused by ultraviolet radiation characterized by applying on the skin or the skin appendages to be treated, a composition comprising said peptide compound.

The following examples describe and demonstrate the efficacy of peptide compounds as described in the invention, but must not be interpreted as limiting the present invention.

Example 1

Study of the Expression of p150Glued in Human Skin Biopsies in the Presence of Peptide SEQ ID NO: 7

The purpose of this study was to assess the influence of the peptide compound SEQ ID NO: 7 on the amount of the subunit of dynactin called p150Glued in human skin biopsies.
Protocol:

Samples of ex-vivo human skin biopsies from a 39 year old female, were cultured at the air/liquid interface. The samples were treated twice a day with a stock solution of peptide SEQ ID NO: 7 at 100 ppm, diluted at the 1%, for 48 hours.

Immunostaining was then performed by means of an antibody directed to p150Glued subunit (REF.Santacruz sc-9804), followed by a secondary antibody, coupled with a green fluorescent marker (REF Invitrogen, A11055). The skin sections were then examined using Nikon® Eclipse 80i microscope.

Quantification was carried out with VOLOCITY® image analysis software.

Results:

An increase by 80% of the dynactin subunit p150Glued staining was observed on the biopsies treated 48 hours with the peptide compound SEQ ID NO: Tat 1%.

Conclusions:

The peptide compound SEQ ID NO: 7 leads to an increase of the expression of the dynactin subunit p150Glued after 48 hours of treatment.

Example 2

Effect of Peptide Compound SEQ ID NO: 7 on Keratinocytes Containing Melanosomes after Treatment with p150Glued siRNA Aim of the Experiment:

The knockdown of dynactin p150Glued expression by a synthetic siRNA was reported to disrupt skin microparasols and to slow down the transfer of melanosomes from melanocytes to keratinocytes (Byers et al., J Invest Dermatol. 2007 July; 127(7):1736-44) The objective of this study was to inhibit dynactin p150Glued expression and investigate the effects of the peptide compound SEQ ID NO: 7 on keratinocytes containing melanosomes.

Cell Culture:

Normal human primary keratinocytes (NHK) and normal human epidermal melanocytes (NHEM) were co-cultured (ratio: 1 melanocyte/4 keratinocytes) in Keratinocyte Serum Free Medium (KSFM, GIBCO) supplemented with 50 µg/ml bovine pituitary extract, 5 ng/ml human recombinant EGF (GIBCO) and 100 µg/ml Primocin™ (INVIVOGEN). Cells were maintained at 37° C. in a humidified atmosphere containing 5% $CO_2$.

Treatments:

NHK and NHEM cells co-seeded for 48 hours were treated, or not, in duplicate, once with 10 nM of p150Glued-specific siRNA.

Cells were then treated, or not, in duplicate, twice a day for 48 hours with a solution of peptide compound SEQ ID NO: 7 at 100 ppm, diluted at 0.5% or 1% before use, without medium change.

Immunolabeling:

Cells were rinsed with PBS and fixed with cold methanol for 4 minutes. Cellular membranes were permeabilized using 0.1% X-100 Triton (Fisher Scientific) for 10 minutes. Unspecific binding sites were blocked, then cells were incubated with the primary antibodies directed to melanosomes (mouse monoclonal anti-"pmel17" Abcam, ab34165 and rabbit monoclonal anti "keratin-14" Abcam, ab51054) diluted in PBS, for 1 hour and a half, under agitation, at room temperature, in a damp room. After three PBS-washes, fluorescent secondary antibody (respectively Alexa Fluor 594 donkey anti-mouse Invitrogen, A21203 and Alexa Fluor 488 donkey anti-rabbit, Invitrogen, A21206) was applied for 1 hour, in the dark, under agitation, at room temperature, in a damp room. After three other washes with PBS, slides were mounted in FLUOROMOUNT-G™ (Electron Microscopy Sciences) for imaging. Detection was managed and examined using a ZEISS AXIOVERT™ 200 M microscope. Photos were taken with a QIMAGING™ EXI blue camera coupled to VOLOCITY™ acquisition software (IMPROVISION™).

Quantification:

Three images per condition were analyzed. For each pictures, total keratinocytes and melanosomes-containing keratinocytes were numerated. The frequency of keratinocyte containing melanosomes was evaluated and expressed in percentage. The mean of the frequencies were used for the graphical representation.

Statistical analyses were performed using Student's t test for independent samples with one-tailed direction of rejection. $p \leq 0.05$ were considered as significant, $p \leq 0.01$ as very significant and $p \leq 0.005$ as highly significant.

Figure 1:
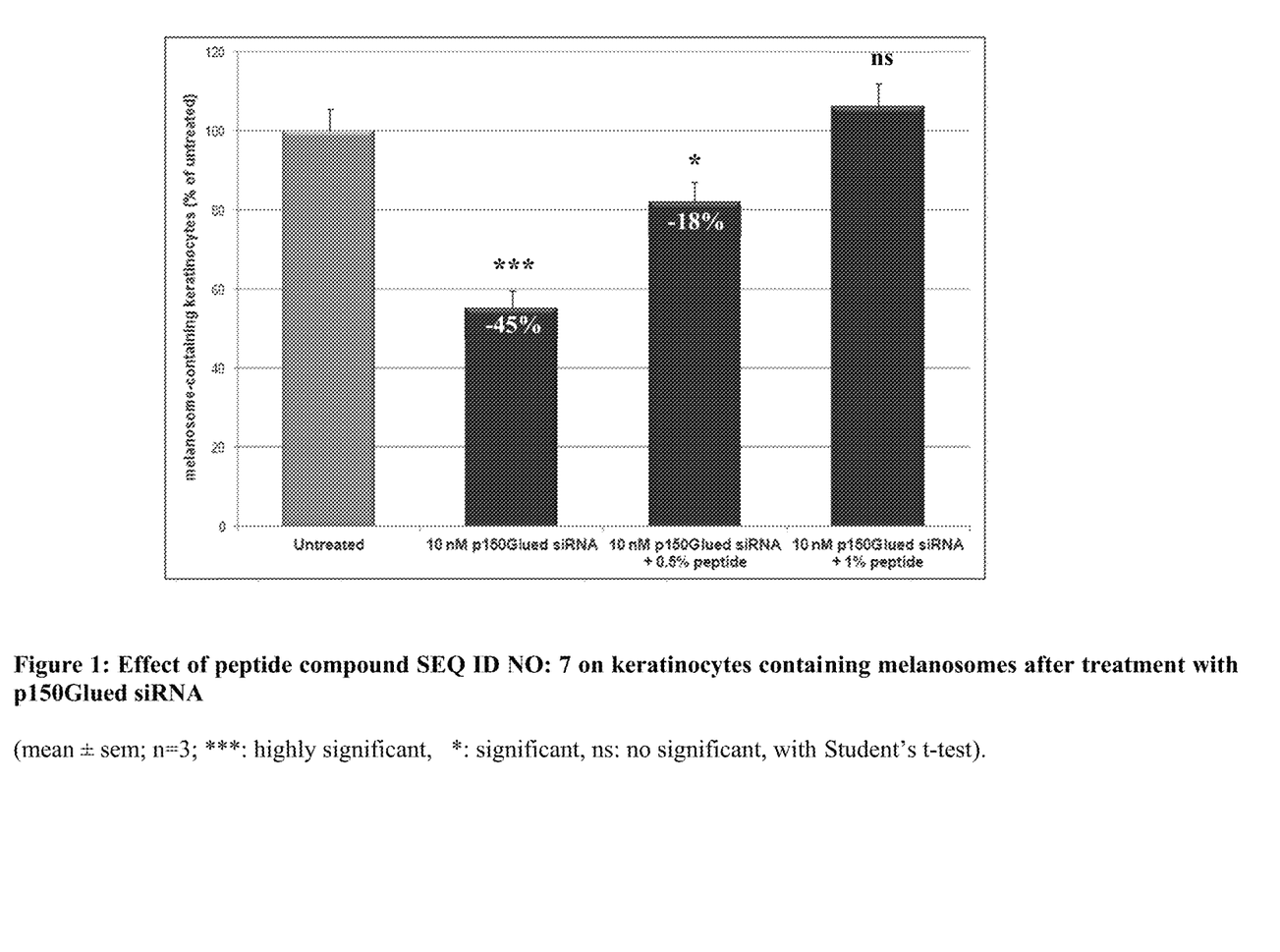
FIG. 1 shows the effect of peptide compound SEQ ID NO: 7 on keratinocytes containing melanosomes after treatment with p150Glued siRNA.

Results:

The results are presented in FIG. 1. In FIG. 1 statistical analyses were expressed versus untreated for peptide compound SEQ ID NO: 7.

NHK treated with 10 nM p150Glued-siRNA presented a decreasing number of melanosome-containing keratinocytes by 45%. However, NHK treated with 0.5% and 1% of peptide compound SEQ ID NO: 7 for 48 hours showed that the frequency of keratinocyte containing melanosomes was respectively partially restored or fully restored when compared to the control.

Conclusion:

A treatment of cells with 0.5% and 1% (respectively 0.5 ppm and 1 ppm) of peptide compound SEQ ID NO: 7 for 48 hours limits the decreasing effect of p150Glued siRNA on the frequency of keratinocytes containing melanosomes.

Example 3

Effect of Peptide Compound SEQ ID NO: 7 on Microparasol Supranuclear Organization Aim of the Experiment:

Provide microscopic analysis of supranuclear organization of melanosomes both by light and electron microscopy:

Skin Culture:

6 mm diameter punch biopsies were obtained from a 25-year-old (light microscopy) and a 39-year-old (electron microscopy) female. They were cultivated on culture medium containing 50% of DMEM 1 g/L glucose (Lonza) and 50% of Ham's-F12 (Lonza) supplemented with 10% of FBS (Lonza), 2 mM of L-glutamine (Lonza) and 100 µg/ml of PRIMOCIN™ (InvivoGen). Skin biopsies were maintained at 37° C. in a humidified atmosphere containing 5% of $CO_2$.

The stock solution of peptide compound SEQ ID NO: 7 was diluted at 0.5% or 1% before use. The biopsies were treated, or not, in duplicate, twice a day with 0.5% (light microscopy) or 1% (electron microscopy) of peptide compound SEQ ID NO: 7 for 48 hours.

Light Microscopy:

After skin culture, tissues were fixed for 4 hours in buffered 10% formalin. Samples were transferred to baths with ethanol progressively concentrated to remove water, then followed by two baths of xylene to remove the alcohol, and finally embedded in molten paraffin wax. Embedded skin biopsies were then cut with a microtome (Shandon) into 4 µm thick sections and placed on SUPERFROST PLUS™ slides (Thermo Scientific).

Fontana-Masson Staining-Light Microscopy:

Sections were deparaffinized and rehydrated with several successive xylene, alcohol and water baths. Then, 100 µl of Stock solution were added on each section and slides were incubated 10 minutes at 60° C. After distilled water wash during 3 minutes, biopsies were incubated with 100 μl of 5% sodium thiosulfate (Sigma) during 2 minutes. Slides were washed during 3 minutes in a distilled water bath and finally dehydrated in several alcohol and xylene baths. They were mounted in Eukitt® (GmbH) and examined using an Eclipse E600 microscope (Nikon). Pictures were taken with a Nikon Digital Camera DMX1200C™ and processed by using the ATC-1C software.

Electron Microscopy:

Ex vivo skin samples were fixed in modified Karnovsky's fixative (Electron Microscopy Sciences) for 1 hour at room temperature and next overnight at 4° C., and then washed in 0.1 M sodium cacodylate buffer (Sigma) Skin samples were then post-fixed in 1% osmium tetroxide in phosphate buffer for 1 hour, rinsed with the buffer, and dehydrated using a graded series of ETOH. The samples were routinely infiltrated with, and embedded in a low viscosity Epon-Epoxy mixture. Sections were cut on an ultramicrotome using a diamond knife, picked up on copper grids, double stained with Uranyl acetate and lead citrate, and examined and photographed under a Transmission Electron microscope operating at 60 KV.

Results:

Pictures of ex-vivo skin reveal a better supranuclear organization of melanosomes above the nucleus after treatment with peptide compound SEQ ID NO: 7 for 48 hours.

Conclusion:

The treatment with peptide compound SEQ ID NO: 7 for 48 hours lead to an improvement of the supranuclear organization of melanosomes above the nucleus.

Example 4

Comet Assay on NHK and NHEM Cells Treated with the Peptide Compound SEQ ID NO: 7 at 1% and Irradiated with Ultraviolet B Radiation (UVB)

Aim of the Experiment:

To assess the protective effect of the peptides according to the invention on NHK and NHEM cells, a comet assay was performed by submitting said cells to UVB radiation.

Cell Culture:

NHK and NHEM were placed in culture for 24 hours in the presence of a solution of peptide compound SEQ ID NO: 7 at 50 ppm diluted at 1% before use, then irradiated with UVB radiation in an amount of 30 mJ/cm$^2$ for NHEM and 60 mJ/cm$^2$ for NHK. A control condition was also used without a peptide active agent. The cells were then detached from their support by trypsin, then centrifuged at 900 rpm for 5 minutes in order to concentrate them and count them.

A defined number of cells (25,000 cells) was then embedded in a Low Melting agarose gel at 0.75%, then deposited on a glass slide previously coated with 1% agarose. The slides were then immersed in a lysis solution for 1 hour 30 minutes at 4° C., then in an alkaline solution for 20 minutes at 4° C. The cells were thus lysed and the DNA was denatured. The slides were immersed in an electrophoresis solution before an electric field (20 V-250 mA) is applied. The DNA thus denatured was subjected to migration in the agarose gel at 4° C. The application of a fluorescent DNA dye on the slides (propidium iodide at 2 μg/ml) makes it possible to observe, under the microscope, DNA appearing in the form of comets if it has been damaged.

Finally, quantification software makes it possible to determine the Tail Moment, means applied to each condition tested. This parameter provides information on the degree of DNA damage: the higher it is the greater the DNA damage.

Figure 2A:
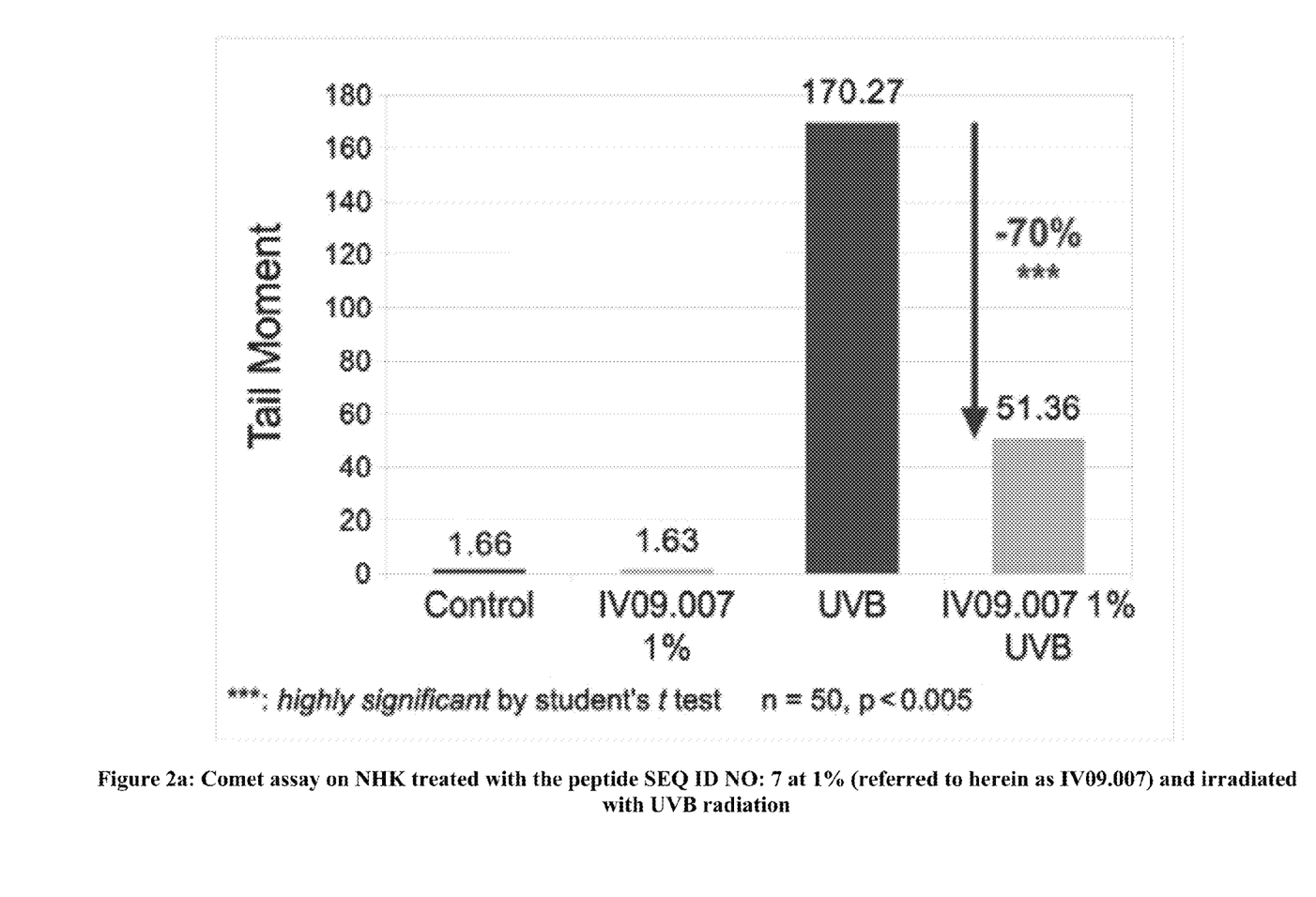
FIGS. 2a and 2b are histograms showing the results of two comet assays performed on normal human keratinocytes (NHK) and normal human epidermal melanocytes (NHEM) subjected to ultraviolet B radiation and treated or not treated with the peptide compound SEQ ID NO: 7.
Figure 2B:
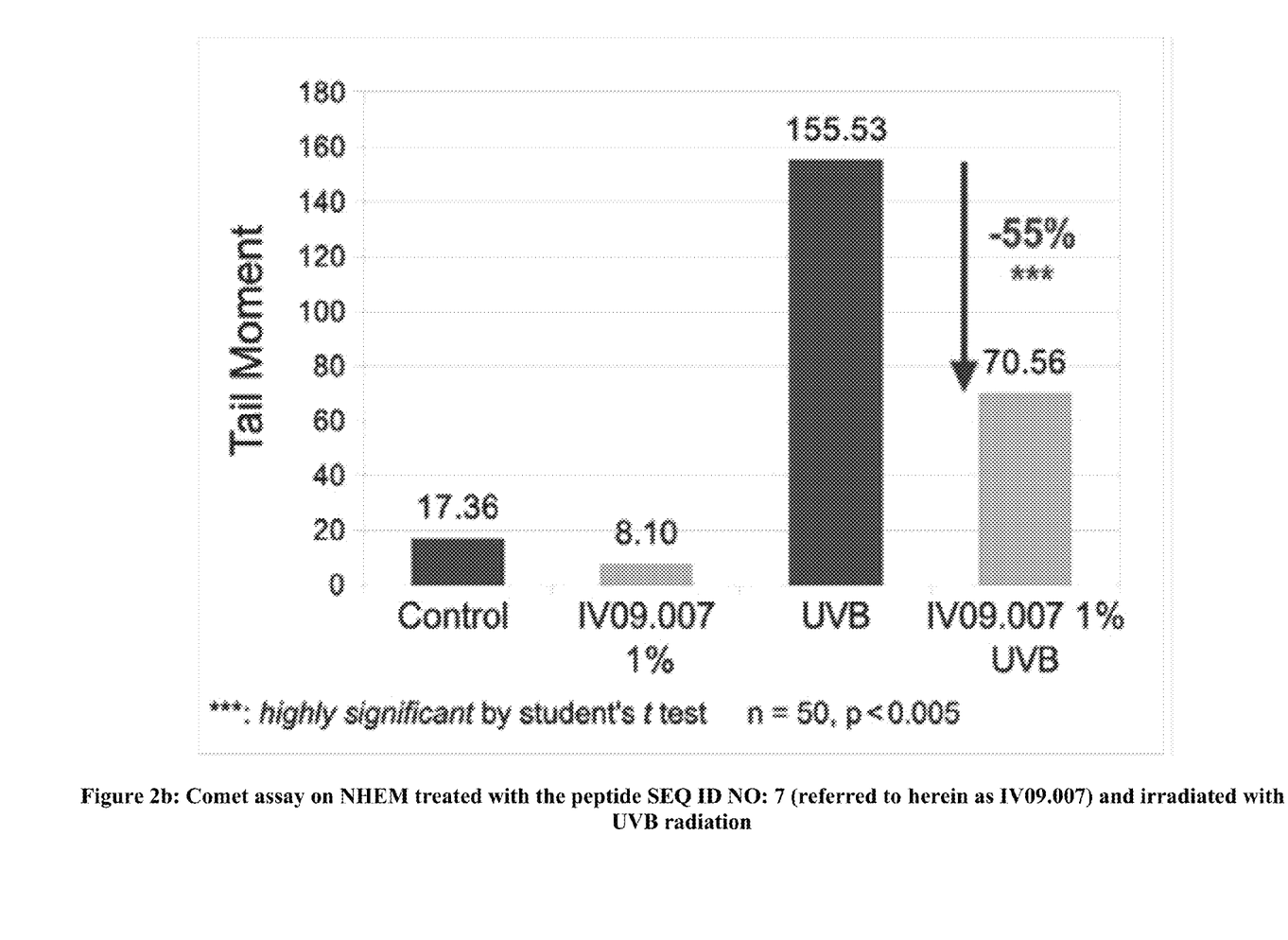

Results:

The results are presented in FIGS. 2a and 2b. FIG. 2a shows the Tail Moment of a comet assay performed on NHK cells. FIG. 2b shows the Tail Moment of a comet assay performed on NHEM cells.

For the NHK, it is observed that, in the presence of UVB, the Tail Moment is very high (170.27 compared with 1.66 in the control). This demonstrates the deleterious effects of UVB radiation on cell DNA. An equivalent result is observed in the NHEM cells. By contrast, when the peptide compound SEQ ID NO: 7 is applied in a pretreatment on the cells, before treatment by UVB radiation, a reduction is observed in the Tail Moment in the NHK, going from 170.27 in the UVB condition to 51.36 in the active agent+UVB condition, i.e. a 70% reduction. A 55% reduction is observed in the NHEM cells.

Conclusions:

The results of these comet assays confirm those obtained in the microarray assay. The peptide compound SEQ ID NO: 7 at 1% (0.5 ppm) made it possible to have a protective action on the cell DNA and, in general, has a protective action against oxidative stresses.

Example 5

Effect of Peptide Compound SEQ ID NO: 7 on the Amount of Cyclobutane Pyrimidine Dimers (CPDs), in Melanocytes after Irradiation with Ultraviolet B Radiation (UVB)

DNA damages induced by UVB radiation can be monitored by quantifying the amount of cyclobutane pyrimidine dimers (CPDs), which are formed after conformational changes in the DNA structure. These DNA lesions alter the structure of DNA and consequently inhibit polymerases and arrest replication. The quantification of CPDs was carried out by immunohistochemical assay.

Protocol:

NHEM (normal human epidermis melanocytes) were grown in Melanocyte Growth Medium (PromoCell) supplemented with 1 ng/ml human basic fibroblast growth factor, 52 μg/ml medium bovine pituitary extract, 0.5 μg/ml hydrocortisone, 5 μg/ml human recombinant insulin, 10 ng/ml phorbol 12-myristate 13-acetate (PMA) and 100 μg/ml of PRIMOCIN (In vivoGen). When the cells were sub-cultured for the experiment, the same medium depleted in PMA was used. Cells were maintained at 37° C. in a humidified atmosphere containing 5% of $CO_2$.

Cells were treated, or not, in duplicate, twice a day for 48 hours with a solution of peptide compound SEQ ID NO: 7 at 100 ppm, diluted at 0.5% or 1% before use. Then, they were irradiated, or not, with a 75 mJ/cm$^2$ UVB dose using a specific oven to ensure the homogeneity of the treatment. They were incubated again during 24 hours without treatment.

Cells were rinsed with PBS and fixed with 3.7% paraformaldehyde, then cellular membranes were permeabilized with Triton X-100 (Fisher Scientific. DNA was denatured with 2

M HCl for 30 minutes. Unspecific binding sites were blocked with 20% FBS (Sigma) solution for 30 minutes at 37° C. Cells were then incubated with the primary antibody (mouse monoclonal anti-"CPD", MBL, D194-1) diluted in PBS containing 5% FBS, under agitation, at room temperature, in a damp room. After washes, fluorescent secondary antibody (Alexa Fluor 488 donkey anti-mouse (Invitrogen, A21202) was applied for 1 hour. Finally, cell nuclei were stained with DAPI at 0.3 µM (Molecular Probes) for 5 minutes and slides were mounted in FLUOROMOUNT-G™ (Electron Microscopy Sciences) for imaging. Detection was managed and examined using a Nikon Eclipse 80i microscope with a 40× objective. Photos were taken with a QIMAGING EXI™ blue camera and processed by using the Q-Capture Pro 7 (QImaging®) acquisition software.

Quantification:

Three images per condition were analyzed. Each picture was converted in grey levels and analyzed with Image-Pro Analyzer 6.3 software (MediaCybernetics, Inc.) which generated a histogram representing the number of pixels per intensity. The sum of all intensities was calculated. Finally, the sum obtained was adjusted by considering the cell number.

Statistical analyses were performed using Student's t test for independent samples with one-tailed direction of rejection. $p \leq 0.05$ were considered as significant, $p \leq 0.01$ as very significant and $p \leq 0.005$ as highly significant.

Figure 3:
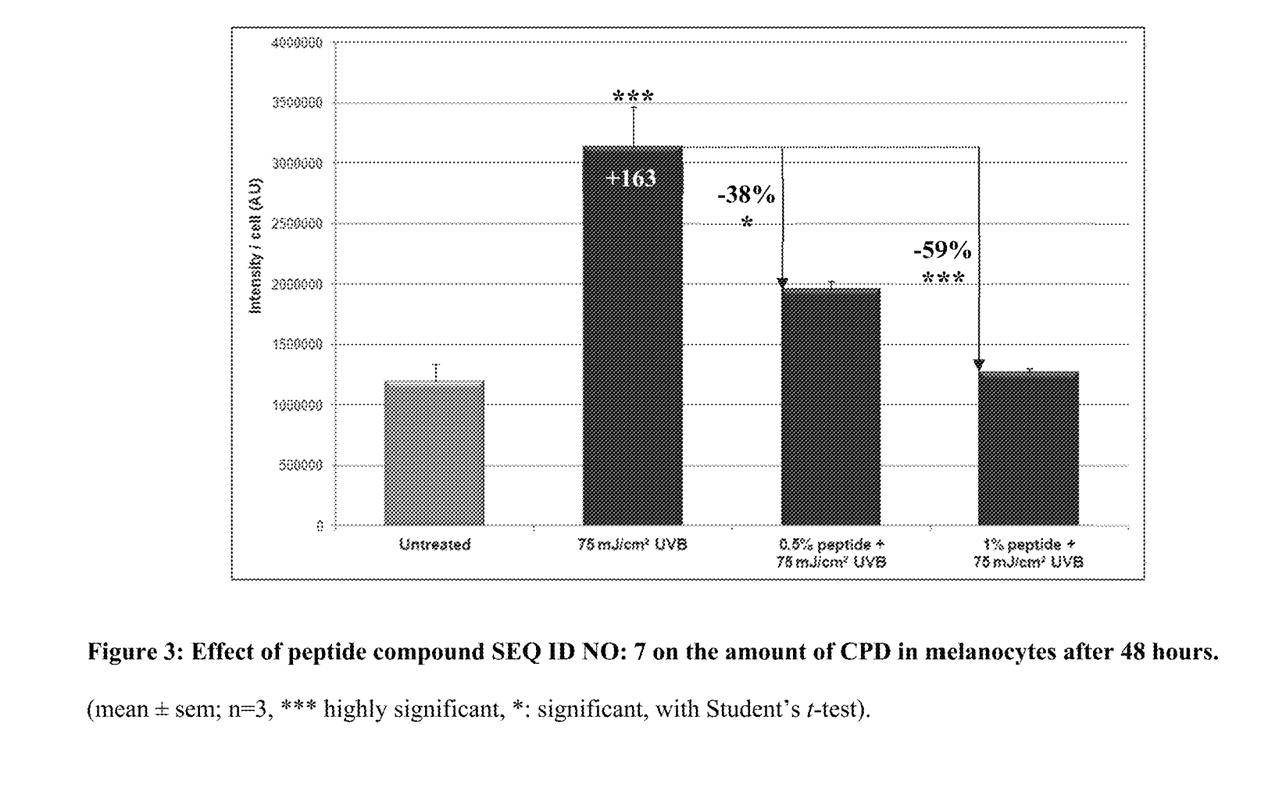
FIG. 3 shows the effect of peptide compound SEQ ID NO: 7 on the amount of CPD in melanocytes after ultraviolet B radiations.

Results:

The results are presented in FIG. 3. In FIG. 3 statistical analyses were expressed versus untreated in grey and versus UVB in black for peptide compound SEQ ID NO: 7.

CPDs increased by 165% in NHEM after irradiation with UVB in non treated conditions when compared to the control. However, when NHEM were pretreated 48 hours with 0.5% or 1% (respectively 0.5 ppm and 1 ppm) of peptide compound SEQ ID NO: 7, UVB radiation induced an increase of CPDs of respectively −39% or −59% when compared to the non treated condition.

Conclusion:

The application of peptide compound SEQ ID NO: 7 limits DNA damages caused by UVB radiation in human normal epidermal melanocytes.

Example 6

Composition of a Sun Cream

| Trade names | INCI names | Weight percent |
|---|---|---|
| PHASE A | | |
| Demineralized water | Aqua (Water) | qs |
| PEMULEN ™ TR1 | Acrylates/C10-30 Alkyl Acrylate Crosspolymer | 0.40 |
| Glycerin | Glycerin | 3.00 |
| NIPAGIN ® M | Sodium Methylparaben | 0.3 |
| PHASE B | | |
| PARSOL ® MCX | Ethylhexyl Methoxycinnamate | 7.50 |
| EUSOLEX ® 4360 | Benzophenone-3 | 3.00 |
| PARSOL ® 1789 | Butyl Methoxydibenzoylmethane | 2.00 |
| MYRITOL ® 318 | Caprylic/Capric Triglyceride | 4.00 |
| EMULGADE ® SEV | Hydrogenated Palm Glycerides (and) Ceteareth-20 (and) Ceteareth-12 (and) Cetearyl Alcohol | 5.00 |
| PHENOZETOL ® | Phenoxyethanol | 0.5 |
| NACOL ® 16-98 | Cetyl Alcohol | 1.00 |
| PHASE C | | |
| TEA | Triethanolamine | 0.20 |
| PHASE D | | |
| Peptide SEQ ID NO: 4 | | 3 ppm |
| Parfum (Fragrance) | Fragrance | qs |
| Dye | | qs |

Applicants incorporate by reference the material contained in the accompanying computer readable Sequence Listing entitled "11-149USCIP_Sequence_Listing.txt" which was created on Dec. 12, 2014, and is 1,777 bytes in size.

The invention claimed is:

1. A cosmetic method for improving microparasol organization in keratinocytes, the method comprising applying a composition comprising a peptide compound having one of the following sequences:

```
                                              (SEQ ID NO: 1)
Ser-Cys-Arg-Asp-Leu-Lys-Lys-Thr-NH2;
or
                                              (SEQ ID NO: 2)
Asn-Ser-Ser-Lys-Asp-Leu-Lys-Lys-Phe-Val-Ala-NH2;
or
                                              (SEQ ID NO: 4)
Gln-Thr-Arg-Asp-Leu-Lys-Lys-Ser-Pro-Lys-Val-NH2;
or
                                              (SEQ ID NO: 5)
Asn-Lys-Asp-Leu-Lys-Lys-Pro-Met;
or
                                              (SEQ ID NO: 6)
His-Asp-Leu-Lys-Lys-Tyr-NH2;
or
                                              (SEQ ID NO: 7)
Asp-Leu-Lys-Lys-NH2;
and
``` a cosmetically acceptable medium to the appendages or to the affected skin of a subject in need thereof.

2. The method of claim 1, wherein applying the composition comprises either before ultraviolet radiation exposure or after ultraviolet radiation exposure.

3. The method of claim 1, wherein applying the composition protects the treated skin or the treated skin appendages against ultraviolet radiation.

4. The method of claim 1, wherein applying the composition decreases DNA damages caused by ultraviolet radiation in keratinocytes and melanocytes.

5. The method of claim 1, wherein applying the composition attenuates age-related pigmentation defects and the effects of photoaging on the skin.

6. The method of claim 1, wherein applying the composition attenuates age-related pigmentation defects.

7. The method of claim 1, wherein applying the composition decreases skin tone irregularities and unifies skin tone.

8. The method of claim 1, wherein the composition comprises said peptide compound solubilized in one or more physiologically acceptable solvents, selected from the group consisting of water, glycerol, ethanol, propanediol, butylene glycol, dipropylene glycol, ethoxylated or propoxylated diglycols, cyclic polyols, or any mixture of these solvents.

9. The method of claim 1, wherein the composition comprises said peptide compound at a concentration of between approximately 0.01 and 5 parts per million (ppm).

10. The method of claim 1, wherein the composition comprises, in addition to the said peptide compound, one or more other active ingredients selected from the group consisting of sunscreens, ultraviolet and Infrared screens, anti-free radical agents, DHEA (dehydroepiandrosterone), vitamin A, retinoic acid, retinol, retinol proprionate retinol palmitate, vitamin B3, niacinamide, niconitate of tocopherol, vitamin B5, vitamin B6, vitamin B12, panthenol, vitamin C, ascorbyl glucoside, ascorbyl tetrapalmitate, magnesium, sodium ascorbyl phosphate, vitamin E, vitamin F, vitamin H, vitamin K, vitamin PP, coenzyme Q10, metalloproteinase inhibitors, activators of TIMP, arginine, ornithine, hydroxyproline, hydroxyproline dipalmitate, palmitoylglycine, hydroxylysine, methionine and its derivatives, Nacylated aminoacids, natural or synthetic peptides, including, di-, tri-, tetra-, penta- and hexapeptides and their lipophilic derivatives, isomers and complex of peptides with metallic ions and notably copper, zinc, manganese or magnesium, peptidic plant extracts obtained by hydrolysis or any other methods, yeast extract, *artemia salina* extract, dehydroacetic acid (DHA), natural or synthetic phystosterols, alpha- and beta-hydroxyacids, silanols, sugar amines, glucosamine, D-glucosamine, N-acetyl-glucosamine, N-acetyl-D-glucosamine, mannosamine, N-acetyl mannosamine, galactosamine, N-acetyl galactosamine, polyphenols, isoflavones, flavonoids, polyphenolic grape polyphenolic extract, pine extract, polyphenolic olive extract, ceramides, phospholipids, squalenes, squalanes, almond oil, coconut oil, castor oil, jojoba oil, olive oil, rapeseed oil, peanut oil, sunflower oil, wheat germ oil, corn germ oil, soybean oil, cotton oil, alfalfa oil, poppy oil, pumpkin seed oil, evening primrose oil, millet oil, barley oil, rye oil, safflower oil, passion oil, hazelnut oil, palm oil, apricot kernel oil, avocado oil, calendula oil, ethoxylated vegetable oils, and shea butter.

* * * * *